US012685566B2

(12) United States Patent　(10) Patent No.:　US 12,685,566 B2
Goldstein et al.　(45) Date of Patent:　Jul. 21, 2026

(54) CRANIAL SPRING APPARATUS AND METHODS

(71) Applicant: University of Pittsburgh—Of the Commonwealth System of Higher Education, Pittsburgh, PA (US)

(72) Inventors: Jesse A. Goldstein, Pittsburgh, PA (US); Justin Beiriger, Pittsburgh, PA (US); Henry Weinrieb, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 2 days.

(21) Appl. No.: 18/917,722

(22) Filed: Oct. 16, 2024

(65) Prior Publication Data

US 2025/0032261 A1　Jan. 30, 2025

Related U.S. Application Data

(63) Continuation of application No. PCT/US2023/020065, filed on Apr. 26, 2023.

(Continued)

(51) Int. Cl.
*A61B 17/68*　(2006.01)
*A61F 2/28*　(2006.01)
(Continued)

(52) U.S. Cl.
CPC ............ *A61B 17/688* (2013.01); *A61B 17/68* (2013.01); *A61F 2/2875* (2013.01);
(Continued)

(58) Field of Classification Search
CPC . A61B 2017/564; A61B 17/688; A61B 17/82; A61B 17/88; A61B 17/8861; A61F 2/2875
See application file for complete search history.

(56) References Cited

U.S. PATENT DOCUMENTS 5,569,250 A * 10/1996 Sarver ..................... A61L 31/06
606/53
5,993,448 A 11/1999 Remmler
(Continued)

FOREIGN PATENT DOCUMENTS

WO　WO 2007/064257　6/2007
WO　WO 2015/133967　9/2015

OTHER PUBLICATIONS

Chan et al., "Endoscope-assisted versus open repair of craniosynostosis: a comparison of perioperative cost and risk," *J Craniofac Surg.*, vol. 24, No. 1, pp. 170-174 (Jan. 2013).
(Continued)

*Primary Examiner* — Larry E Waggle, Jr.
(74) *Attorney, Agent, or Firm* — Klarquist Sparkman, LLP

(57) ABSTRACT

A cranial spring for treatment of craniosynostosis includes two arms that extend from a center point or center portion and have a space or gap disposed between end portions of the arms. Each of the arms can include a foot portion configured to distribute a spring force over a wider surface area of bone relative to conventional cranial springs. In some examples, the arms are linear and extend away from a curved central vertex portion, thereby giving the spring an overall U-shape or V-shape configuration. In other examples, the arms are continuously curved thereby giving the spring an overall circular shape. The spring can be formed from a bioresorbable material that is configured to dissolve after implantation over a specified resorption period, and therefore can be used in cranioplasty without requiring a second surgical procedure for removal thereof.

20 Claims, 8 Drawing Sheets

Related U.S. Application Data

(60) Provisional application No. 63/364,024, filed on May 2, 2022.

(51) Int. Cl.
| | |
|---|---|
| *A61B 17/00* | (2006.01) |
| *A61B 17/56* | (2006.01) |

(52) U.S. Cl.
CPC ............... *A61B 2017/00004* (2013.01); *A61B 2017/564* (2013.01); *A61B 2017/681* (2013.01)

(56) References Cited

U.S. PATENT DOCUMENTS

| | | | | |
|---|---|---|---|---|
| 6,197,037 | B1 * | 3/2001 | Hair | ..................... A61B 17/688 606/151 |
| 8,206,425 | B2 | 6/2012 | Khanna | |
| 8,241,336 | B2 * | 8/2012 | Ralph | .................. A61B 17/688 606/281 |
| 9,827,012 | B2 * | 11/2017 | Nakaji | ............... A61B 17/8061 |
| 10,548,636 | B2 | 2/2020 | Gordon et al. | |
| 11,457,955 | B2 * | 10/2022 | Garcia | ............... A61B 17/8061 |
| 11,504,161 | B2 | 11/2022 | Khanna et al. | |
| 2014/0336716 | A1 * | 11/2014 | Seegert | .................. A61B 17/68 606/86 R |
| 2017/0296243 | A1 | 10/2017 | Dunaway et al. | |
| 2022/0259781 | A1 * | 8/2022 | Kulkova | .................. D04C 1/06 |
| 2022/0346839 | A1 | 11/2022 | El Amm | |

OTHER PUBLICATIONS

Eppley et al., "Resorbable plate fixation in pediatric craniofacial surgery," *Plast Reconstr Surg*, vol. 100, No. 1, pp. 1-7 (Jul. 1997).

Faller et al., "Development and testing of an absorbable spring for cranial expansion in rabbits," *Journal of Cranio-Maxillofacial Surgery*, vol. 43, No. 7, pp. 1269-1276 (Sep. 2015).

International Search Report and Written Opinion dated Jul. 17, 2023, from International Patent Application No. PCT/US2023/020065, 14 pp.

Pyle et al., "Spring-assisted surgery-a surgeon's manual for the manufacture and utilization of springs in craniofacial surgery," *J Craniofac Surg.*, vol. 20, No. 6, pp. 1962-1968 (Nov. 2009).

* cited by examiner

1

CRANIAL SPRING APPARATUS AND METHODS

CROSS-REFERENCE TO RELATED APPLICATIONS

This application is a continuation of International Patent Application No. PCT/US2023/020065, filed Apr. 26, 2023, which claims the benefit of U.S. Provisional Patent Application No. 63/364,024, filed May 2, 2022, each of which is incorporated by reference herein in its entirety.

FIELD

The present disclosure relates to implantable spring apparatus, such as implantable cranial springs configured for treatment of craniosynostosis, and related methods or use and manufacture thereof.

BACKGROUND

Cranial sutures are the joints between a baby's skull bones that comprise flexible, fibrous tissue and function to allow the skull to expand during growth of the baby's brain. Sutures are the primary location for skull expansion that occurs as a result of rapid brain growth in the first two years of life. After this time, other skull growth mechanisms become dominant. However, cranial sutures normally remain "open" (relatively flexible) through the second decade of life.

Craniosynostosis is a birth defect in which bones in a baby's skull fuse prematurely during development. In a baby with craniosynostosis, one or more of the sutures closes or fuses too early. This can limit or slow the development of the baby's brain as the skull is unable to expand rapidly enough to accommodate brain growth. Additionally, because the fused bones are unable to expand as the brain grows, skull growth is directed to other (open) sutures, resulting in head shape deformities which follow distinct patterns depending on which suture is fused. If left untreated, there is a significant risk of increased pressure developing inside the skull (intracranial pressure) which can lead to headaches, developmental delay, and/or blindness.

Almost half of cases of craniosynostosis involve fusion of the sagittal suture (which can occur 1 in 4000 live births). The sagittal suture runs along the top of the head, from the baby's soft spot near the front of the head to the back of the head. In sagittal craniosynostosis (SC), the infant's head becomes progressively misshapen (e.g., elongated in posterior direction) due to the growth restriction across the sagittal suture which prevents skull widening. Most children born with sagittal craniosynostosis require surgical intervention to laterally expand the skull and normalize the head shape.

There are a variety of different treatment paradigms to address SC that range from open surgical procedures, which completely reshape the infant head and can result in long hospital stays and large scars, to less invasive procedures, which rely on post-operative molding to reshape the head. A commonly employed technique involves removing the abnormal suture and placing the child in a helmet for a year to passively reshape the head. This relies on patients and their caregivers using the helmet as directed, which has been shown to have a significant non-compliance rate. Additionally, helmet treatment works by gently compressing the skull where it is prominent in order to direct growth toward areas where the skull is deficient. This may cause additional pressure on the brain and may be uncomfortable and/or painful to the patient.

Spring cranioplasty (also termed "spring-assisted cranioplasty" or "spring-assisted synostosis" surgery) is a minimally invasive surgical technique that can be performed to correct specific cranial deformities caused by craniosynostosis. In such procedures, the abnormal cranial suture is excised surgically and one or more springs of a known force (commonly two or three springs) are placed in the suture gap to widen the skull over time in a direction perpendicular to the axis of the excised suture. As the springs expand, they can normalize the head shape and create more space for brain growth. This technique has gained in popularity over the last decade, due in part to being less invasive than other surgical techniques and having improved compliance over helmet techniques.

Typical cranioplasty procedures utilize metal springs that can be pre-fabricated or custom-made by the surgeon pre-operatively from stainless steel k-wires. A known stainless-steel cranial spring is shown FIG. 1A, and FIG. 1B illustrates placement or implantation of two stainless-steel springs in tandem in an opposing orientation along a sagittal suture gap during a cranioplasty procedure.

These stainless steel springs must be removed from the patient in a second operative procedure which usually takes place several months after spring placement.

SUMMARY

Disclosed herein are implantable cranial springs configured for treatment of craniosynostosis, and related methods. The disclosed cranial springs and methods provide improvements over conventional technology and solve many of the problems associated with the convention technology.

In one aspect, a cranial spring is disclosed. The cranial spring can include a first arm and a second arm, each of the first arm and the second arm joined at a center portion, wherein the first arm includes a first end portion and the second arm comprises a second end portion, an opening disposed between first end portion and the second end portion; and a first foot portion disposed at the first end portion, and a second foot portion disposed at the second end portion; wherein the first foot portion is configured to abut a first skull bone, and the second foot portion is configured to abut a second skull bone.

In some examples, each of the first arm and the second arm is continuously curved and forms a semi-circular-shaped body of the cranial spring.

In some examples, the center portion is a curved center portion and each of the first arm and the second arm is linear, the curved center portion, the first arm and the second arm forming a U-shaped body or a V-shaped body of the cranial spring.

In some examples, the cranial spring is made of a bioresorbable material.

In some examples, each of the first arm and the second arm has an H-configuration cross-section.

In some examples, each of the first bone abutment surface and the second bone abutment surface is sized and shaped such that, when the cranial spring is implanted, the cranial spring applies a first spring force on a portion of the first skull bone and a second spring force on a portion of the second skull bone.

In some examples, each of the first bone abutment surface and the second bone abutment surface is sized and shaped such that, when the cranial spring is implanted, a distribution of the first spring force across the portion of the first skull bone limits shear of the first skull bone and a distribution of the second spring force across the portion of the second skull bone limits shear of the second skull bone.

In another aspect, a bioresorbable cranial spring is disclosed. In some examples, the bioresorbable cranial spring includes a first arm and a second arm, each of the first arm and the second arm joined at a center portion, wherein the first arm comprises a first end portion and the second arm comprises a second end portion, an opening disposed between the first end portion and the second end portion, wherein each of the first arm and the second arm has an H-configuration cross-section configured to increase a surface area-to-volume ratio of the bioresorbable cranial spring.

In another aspect, a cranioplasty method is disclosed. In some examples, the method includes accessing a skull of a patient through an incision; excising an abnormal suture to form a suture gap; implanting one or more bioresorbable cranial springs within the suture gap such that a longitudinal axis of the one or more bioresorbable cranial springs is aligned with the suture gap; closing the incision; and allowing the one or more bioresorbable cranial springs to dissolve over a resorption period within the patient without surgical removal thereof.

In some examples, the implanting the one or more bioresorbable cranial springs includes deforming a first arm and a second arm of each of the one or more springs toward the longitudinal axis of the respective spring, engaging a first foot portion at an end portion of the first arm with an edge a first skull bone, and engaging a second foot portion at an end portion of the second arm with an edge of a second skull bone.

The foregoing and other objects, features, and advantages of the disclosed technology will become more apparent from the following detailed description, which proceeds with reference to the accompanying figures.

DETAILED DESCRIPTION

General Considerations

Figures 1A, 1B:
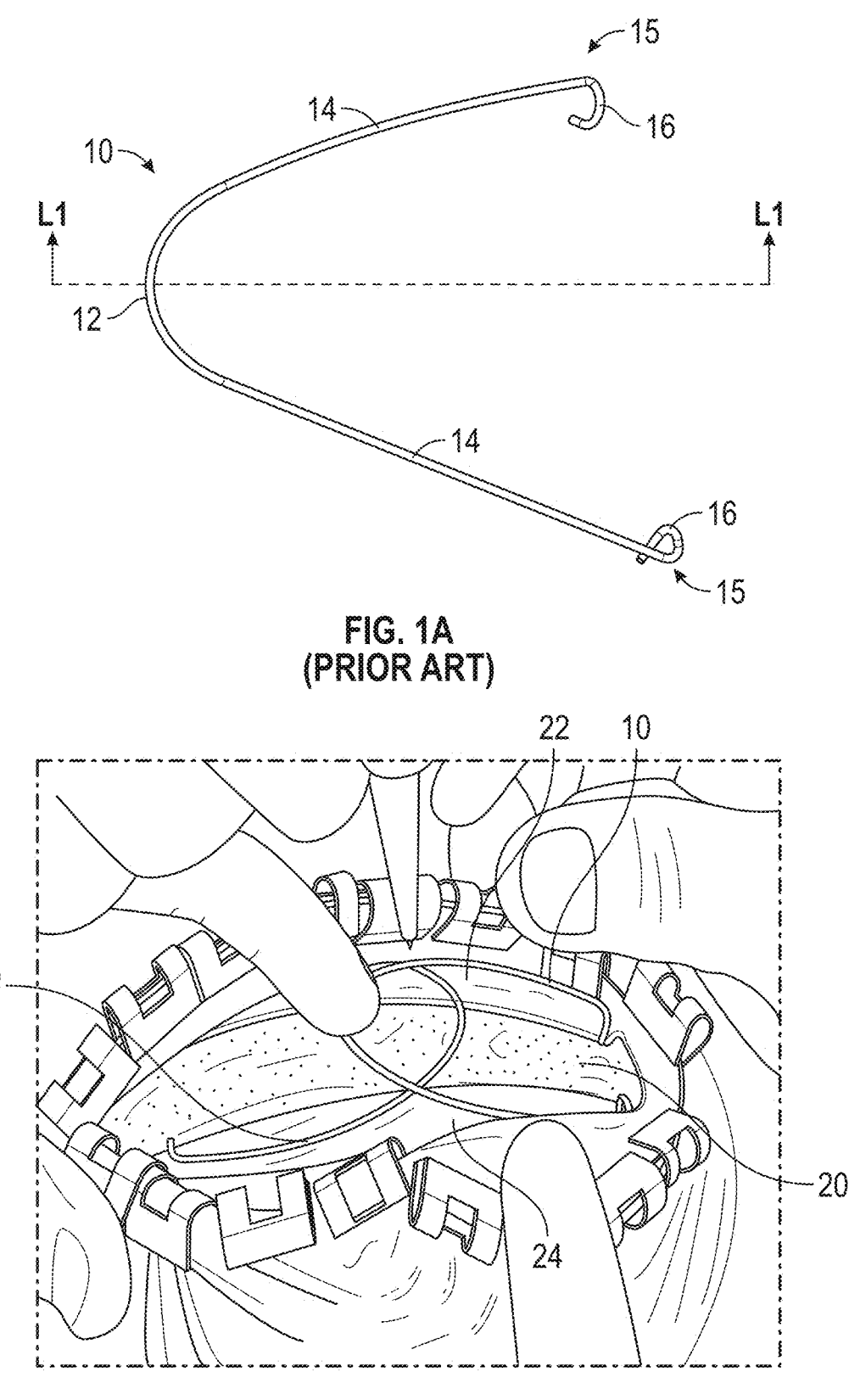
FIG. 1A is a top perspective view of a conventional stainless steel wire cranial spring.
FIG. 1B illustrates an implantation procedure for the cranial spring of FIG. 1A.

For purposes of this description, certain aspects, advantages, and novel features of the examples of this disclosure are described herein. The described methods, systems, and apparatus should not be construed as limiting in any way. Instead, the present disclosure is directed toward all novel and non-obvious features and aspects of the various disclosed examples, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present, or problems be solved.

Features, integers, characteristics, compounds, or materials described in conjunction with a particular aspect, embodiment or example of the disclosure are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The disclosure is not restricted to the details of any examples. The disclosure extends to any novel one, or any novel combination, of the features disclosed in this specification (including any accompanying claims, abstract, and drawings), or to any novel one, or any novel combination, of the steps of any method or process so disclosed.

As used herein, the terms "a," "an," and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A," "B," "C," "A and B," "A and C," "B and C," or "A, B, and C." Further as used herein, "and/or" means "and" or "or," as well as "and" and "or."

As used herein, the terms "coupled" or "attached" generally mean physically coupled or linked and does not exclude the presence of intermediate elements between the coupled or attached items absent specific contrary language.

Directions and other relative references (e.g., inner, outer, upper, lower, etc.) may be used to facilitate discussion of the drawings and principles herein, but are not intended to be limiting. For example, certain terms may be used such as "inside," "outside,", "top," "bottom," "upward," "downward," "interior," "exterior," "distal," "proximal," and the like. Such terms are used, where applicable, to provide some clarity of description when dealing with relative relationships, particularly with respect to the illustrated examples. Such terms are not, however, intended to imply absolute relationships, positions, and/or orientations. For example, with respect to an object, an "upper" part can become a "lower" part simply by turning the object over. Nevertheless, it is still the same part and the object remains the same.

Overview of the Disclosed Technology

As discussed above, known cranioplasty procedures utilize stainless steel springs that can be pre-fabricated or custom-made by the surgeon preoperatively from stainless steel k-wire. A standard stainless-steel cranial spring 10 is formed from stainless-steel wire and includes a generally V-shaped or U-shaped body having a vertex portion 12 and a pair of opposing arms 14 extended away or outward from the vertex portion (FIG. 1A). End portions 15 of each of the arms 14 are outwardly curved (away from a longitudinal axis L1) and extend distally downward (along a vertical axis perpendicular to the longitudinal axis L1) to form wire hook portions 16 at the ends of the arms 14.

As shown in FIG. 1B, in a first surgical procedure, the stainless-steel cranial springs 10, 10' can be implanted within an excised sagittal suture gap 20 in an opposing orientation relative to each other, where the longitudinal axis L1 of each spring is aligned with the suture gap 20 and the vertex portions 12 of the springs 10, 10' are in an overlapping configuration. Further, the wire hook portions 16 at opposing ends of the overlapping springs 10, 10' are hooked over or engaged with edges of skull bones 22, 24 (e.g., the left and right parietal bones) on opposing sides of the sagittal suture 20.

Each of the springs 10, 10' is implanted in a compressed state where the arms 14 are compressed toward each other. In other words, a width of the sagittal suture gap 20 is less than a distance between the distal ends 15 of the arms 14 when the spring 10 is at a resting, fully expanded state. A size and/or material strength of the springs 10, 10' can be selected such that each of the springs acts on the skull bones 22, 24 with a known force in a direction away from the longitudinal axes L1 of the spring. Over time, the springs 10, 10' cooperatively function to widen the skull in a direction generally perpendicular to the axis of the excised suture 20. As the springs expand 10, 10', they can normalize the head shape and create more space along the sagittal suture. After normalization of the head shape over a period of approximately 4 months, a second surgical procedure is performed to remove the springs 10, 10' from the patient.

Figure 2A:
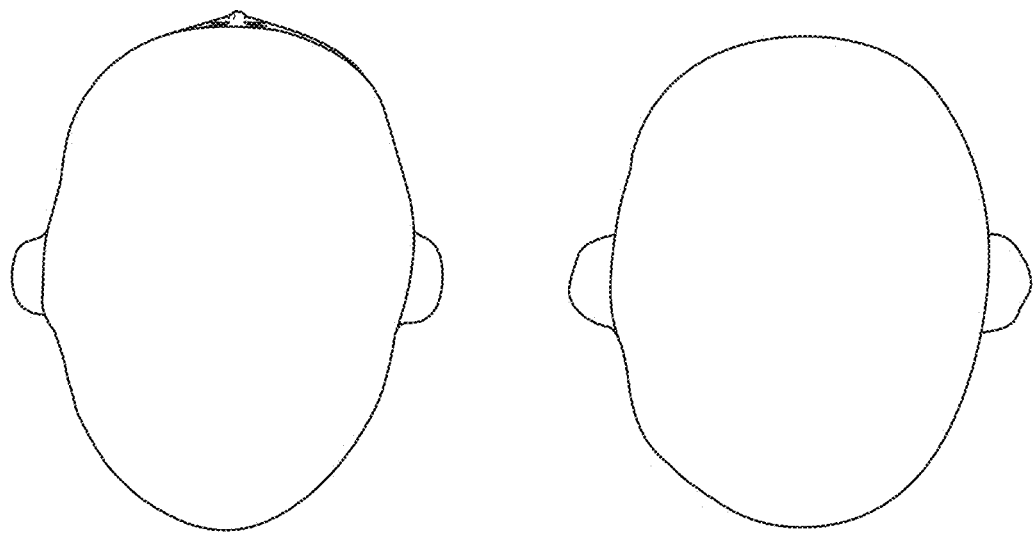
FIG. 2A illustrates a skull shape of a patient having craniosynostosis before and after a cranioplasty treatment.

FIG. 2A shows a top-down view of a child's head before (left) and after (right) after spring-assisted cranioplasty. The anterior portion of the head (the face) is oriented toward the top of the image and a posterior portion of the head is oriented toward the bottom of the image. As can be seen in FIG. 2A, prior to spring-assisted cranioplasty (left), the head has an abnormal (elongated or narrow) shape, and after spring-assisted cranioplasty (right), the head has a normalized (wider) shape.

There are a number of issues or drawbacks to conventional spring-assisted cranioplasty. For example, the stainless-steel cranial springs require the subsequent (second) surgery once the skull has been adequately expanded. While the removal procedure may be less invasive than the original spring placement, it is still a significant surgery for young children with craniosynostosis and can disrupt healing from the initial (first) surgery. There are also concerns that excessive exposure to anesthetics in infancy can lead to neurocognitive impairment. Thus, there is a need for a treatment modality that imparts the same force to the skull without the need for a second operation.

In another example, conventional springs used in the procedure can cause damage to the skull bones by putting excessive pressure on a small portion of the surface area of the bone which can result in "cheese-wiring" of the wire hook portion of the spring through the skull. In other words, the narrow wire forming the hooks of the cranial spring can exert excessive, concentrated force on a small surface area of the skull edge (at the point of contact between the wire hook portion and the edge of the skull bone) and burrow into the skull rather than forcing it to expand. This may be caused by excessive pressure (for example, force per area of contact) on the bone surface at the edge of the skull bone.

Figure 2B:
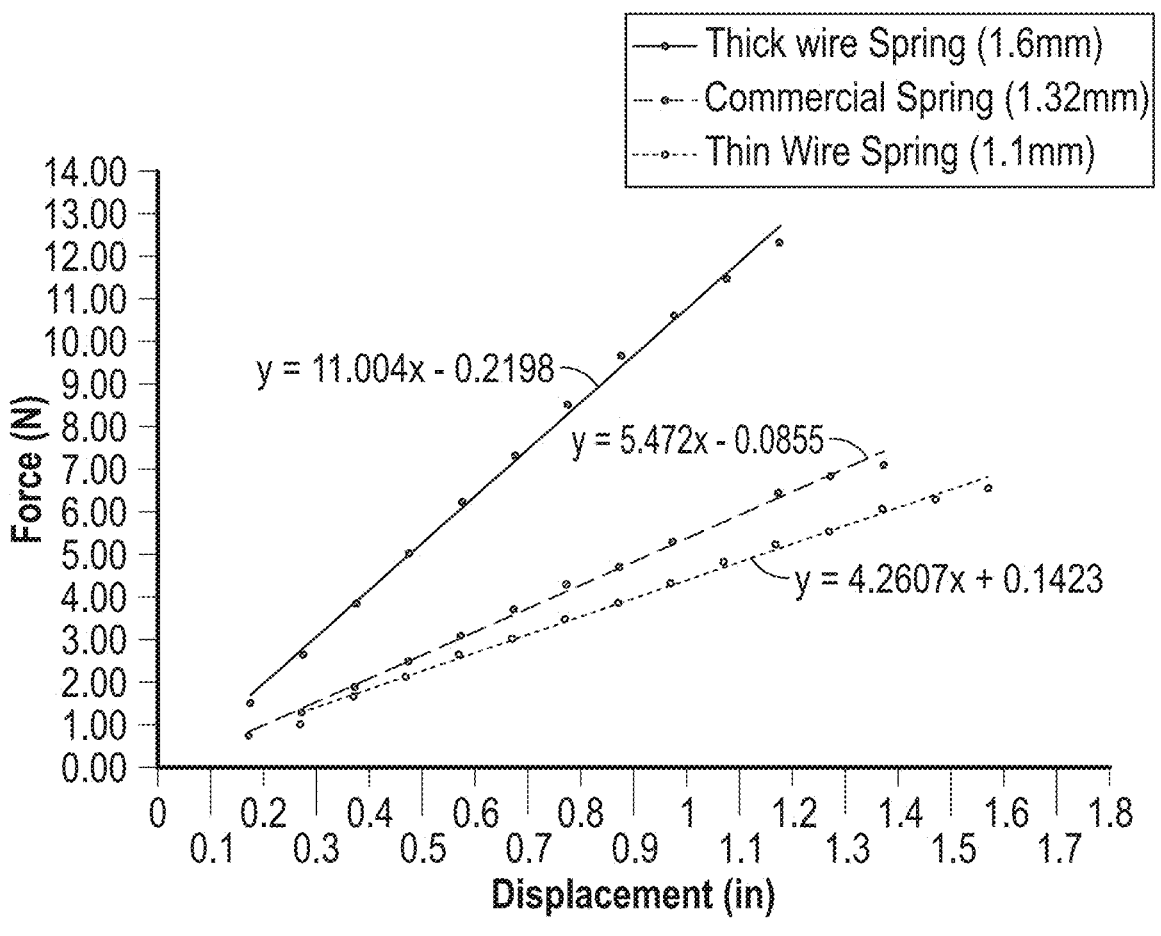
FIGS. 2B and 2C are graphs showing exemplary force-displacement curves for various conventional stainless steel wire cranial springs.
Figure 2C:
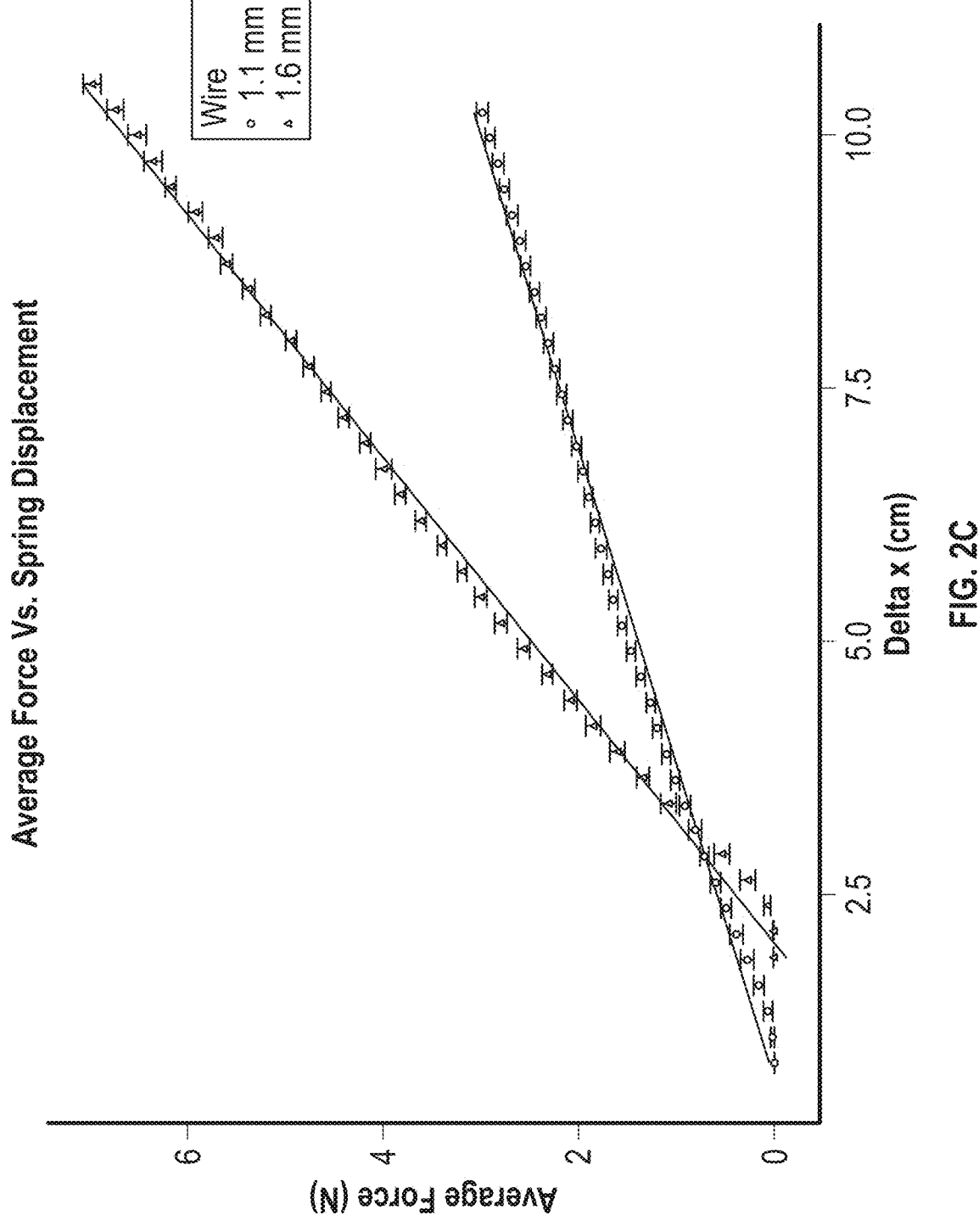

In yet another example, FIGS. 2B and 2C show graphical illustrations of load/force-displacement curves for various stainless steel springs having different properties (i.e., different diameters of the steel wire). As can be seen therein, force and displacement have a linear relationship, and as the force increases for a given spring design, the amount of maximum displacement (expansion) decreases, for example, due to bone shearing or burrowing ("cheese-wiring"). Thus, the maximum spring expansion may be better correlated to cranium expansion than the spring force, and there is a need for springs that can provide sufficient maximum spring expansion in cranioplasty procedures without excessive force.

The cranial springs and surgical methods disclosed herein can address the foregoing issues. In some examples, the cranial springs disclosed herein can be comprised of a bioresorbable material that has elastic and material strength properties sufficient to exert a force on the skull bones of an infant to cause separation, but can be broken down and absorbed by the body. Therefore, in such examples, after a first implantation procedure, the cranial springs may not require manual removal in a second surgical procedure. In one specific example, a cranial spring can be comprised of Poly (D,L-lactide-co-glycolide), 85:15 (referred to as 85:15 PLGA).

Further, in some examples, the cranial springs disclosed herein can have one or more structural features that facilitate a specified rate or time period for bioresorption, a specified spring force, and/or a specified maximum expansion.

Yet further, in some examples, the cranial springs disclosed herein can include a foot portion at the end portions of the arms of the spring to increase a contact surface area between the spring and the skull bone, thereby preventing or limiting cheese-wiring of the spring through the bone.

Further still, in some examples, the cranial springs disclosed herein can have a circular shape that more evenly distributes force across the vertex portion of the spring relative to a U or V-shaped spring, which can prevent or limit breakage or failure of a cranial spring after implantation.

Exemplary Cranial Springs

Figure 3A:
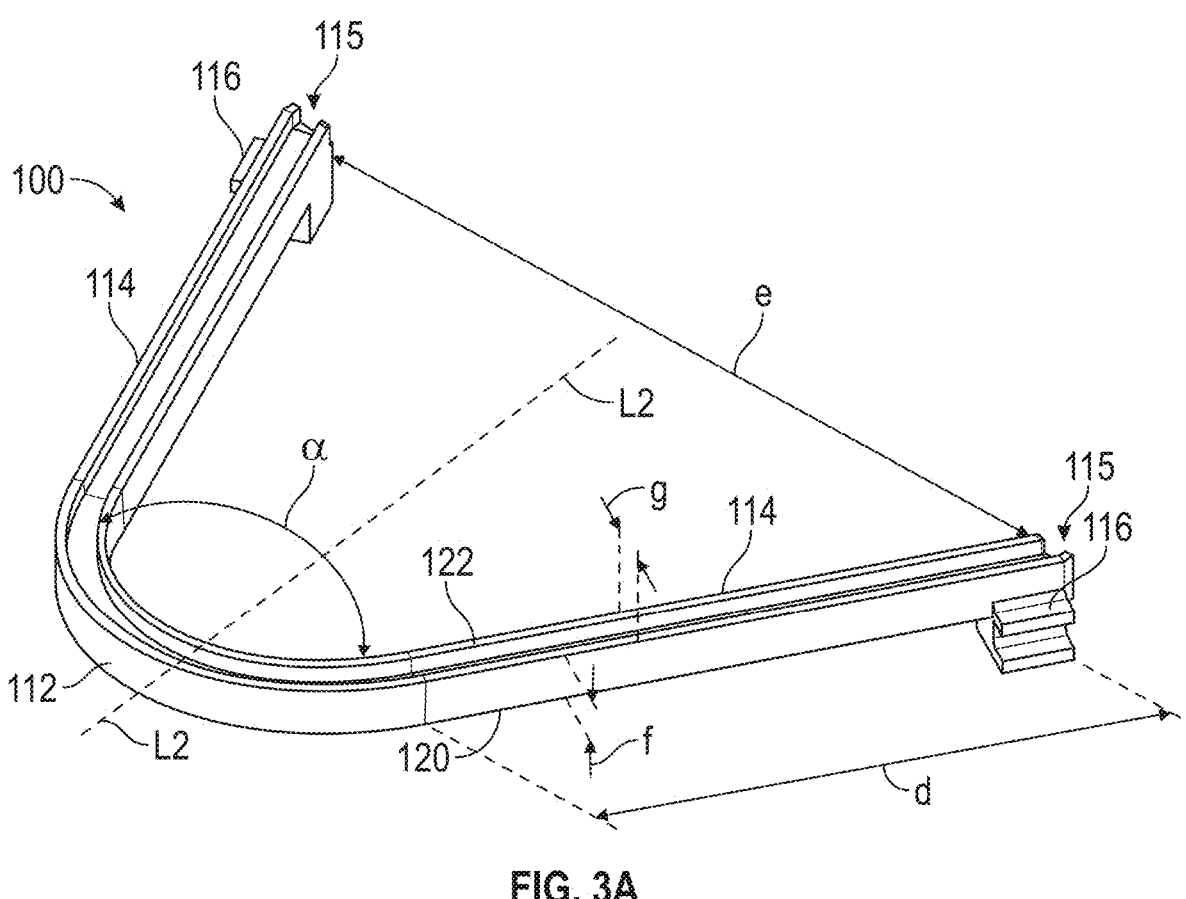
FIGS. 3A and 3B are perspective views of a first exemplary cranial spring.
Figure 3B:
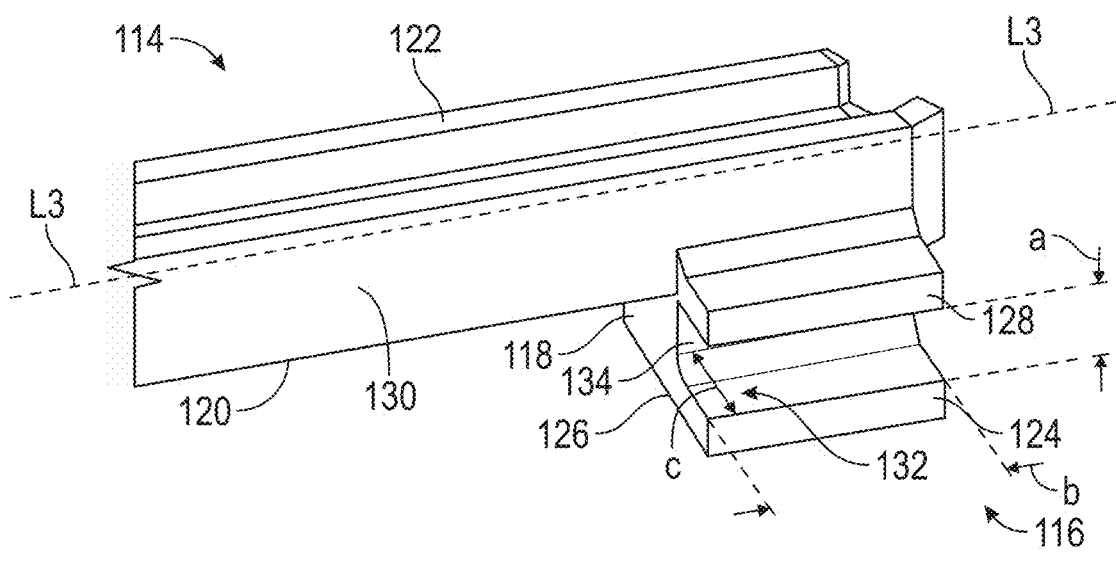

Turning to FIGS. 3A and 3B, a first exemplary cranial spring 100 is shown and described. Specifically, the cranial spring 100 can comprise a generally V-shaped or U-shaped body having a center or vertex portion 112, two linear arms 114 joined to and extending away from the center vertex portion, and foot portions 116 (for example, foot plates, foot hooks, etc.) disposed at end portions 115 of each of the arms 114. In other words, a first foot portion 116 is disposed at a first end portion 115 of a first one of the arms 114, and a second foot portion 116 is disposed at a second end portion 115 of a second one of the arms 114. The foot portions 116 can be attached to or formed on a first (lower) surface 120 of the end portions 115 of the arms 114 and extend outwardly or away from a longitudinal axis L2 of the spring. When implanted, the first (lower) surface 120 can be oriented toward the patient's brain, and an opposing second (upper) surface 122 can be oriented away from the patient's brain.

As can be seen in FIG. 3B, the foot portion 116 can be configured to form an abutment region or an engagement portion of the spring 100 for contact with bone. In some examples, the foot portion 116 can include a base portion 118 that extends from the lower surface 120 along a vertical axis (e.g., along a vertical axis that is perpendicular to a longitudinal axis L3 of the arm 114). A lower extension 124 can project outwardly from the base 118 (in a direction perpendicular to the longitudinal axis L3 of the arm 114) and can be coextensive with a distal surface 126 of the base 118. An opposing upper extension 128 can project outwardly from an exterior side surface 130 of the arm 114 (in a direction perpendicular to the longitudinal axis L3 of the arm 114). Interior surfaces of the pair of extensions 124, 128 and a central surface 134 disposed therebetween form a recess 132 (which can also be referred to as a channel, a receiving portion, or an engagement portion).

When engaged with the skull bone, the interior surfaces of the pair of extensions 124, 128 can be configured to respectively contact exterior and interior surfaces of the bone, and the central surface 134 can be configured to contact a side edge of the bone. Accordingly, the recess 132 of each foot portion 116 can be shaped and sized to engage or receive an edge of a skull bone along a sagittal suture gap. For example, one of the foot portions 116 can engage a first skull bone on a first side of a suture gap (such as, for example, the skull bone 22 on a first side of the suture gap 20 shown in FIG. 1B) for application of a first spring force thereon, and the other of the foot portions 116 can engage a second skull bone on an opposing side of the suture gap (such as, for example, the skull bone 24 on a second side of the suture gap 20 shown in FIG. 1B) for application of a second spring force thereon. As the central surface 134 of the foot portion 116 contacts the side edge of the bone, in some examples, the central surface 134 can be characterized as a bone abutment surface configured to apply a spring force on the bone.

In some examples, the configuration of the foot portion 116 provides a wider surface area for contacting the bone at the top, bottom, and/or side surfaces thereof relative to conventional cranial springs (such as, e.g., the cranial spring 10 shown in FIG. 1A). The relatively wider foot portion (for example, the wider central surface 134) enables distribution of the spring force across a greater surface area of bone relative to conventional cranial springs (which comprise a wire having a narrower width relative to a height thereof), thereby decreasing or limiting or eliminating the risk of bone shear or burrowing while implanted relative to conventional cranial springs. For example, as indicated in FIG. 3B, the surfaces that form the recess 132 are sized such that the recess 132 can have a height a, a width b, and a depth c. In some examples, the height a can be in range from 2 mm to 10 mm, the width b can be in a range from 4 mm to 15 mm, and the depth c can be in a range from 2 mm to 10 mm. When implanted in the cranium of a patient, the width b can extend in the direction of the edge of the adjacent bone, and the height a can extend generally in the direction of the bone thickness. In some examples, the width b can be greater than the height a. For example, the width b can be in a range of 1.5 to 7.5 times greater than the height a, such as being 1.5 to 2 times greater, 1.5 to 3 times greater, 1.5 to 3.5 times greater, 2 to 3 times greater, etc.

Returning to FIG. 3A, a curvature of the vertex portion defines an angle α between the arms 114 and each arm 114 has a length d. Further, the distal ends 115 of the arms 114 have a distance e therebetween (which can be defined by the angle α and the length d and forms an opening or a gap between the arms) when the cranial spring is in a relaxed, unconstrained state. In some examples, the length d can be in a range from 35 mm to 100 mm, the angle α can be in a range from 20 to 70 degrees, and the distance e can be in a range from 40 mm to 90 mm. Further, each of the vertex portion 112 and the arms 114 has a height f and a width g. In some examples, the height f can be in a range of 2 mm to 6 mm and the width g can be in a range of 2 mm to 6 mm.

It will be appreciated that the foregoing dimensions of the spring 100 are merely exemplary, and the recess 132 (and/or other portions of the foot portion 116), as well as the arms 114 and the vertex portion 112 can have other dimensions in alternate implementations. Additionally, the angle α is merely exemplary and can be smaller or larger in alternate implementations.

In some examples, the foregoing features of the spring (dimensions and the angle α) can be selected to provide a specified force, a specified maximum spring expansion, and/or a specified distribution of spring force on bone. Further, in some examples, the foregoing features of the spring (dimensions and the angle α) can have a known or quantifiable relationship to one another and be varied proportionally to meet the specified force, the specified maximum spring expansion, and/or the specified distribution of spring force on bone.

For example, where the angle α is larger, a potential spring force and/or a maximum spring expansion may be increased, and a width of the foot portion can be proportionally increased to meet a specified distribution of the spring force on bone. In another example, where the angle α is smaller, a potential spring force and/or a maximum spring expansion may be decreased, and a width of the foot portion can be proportionally decreased to meet the specified of the spring force on bone.

Figures 4A, 4B:
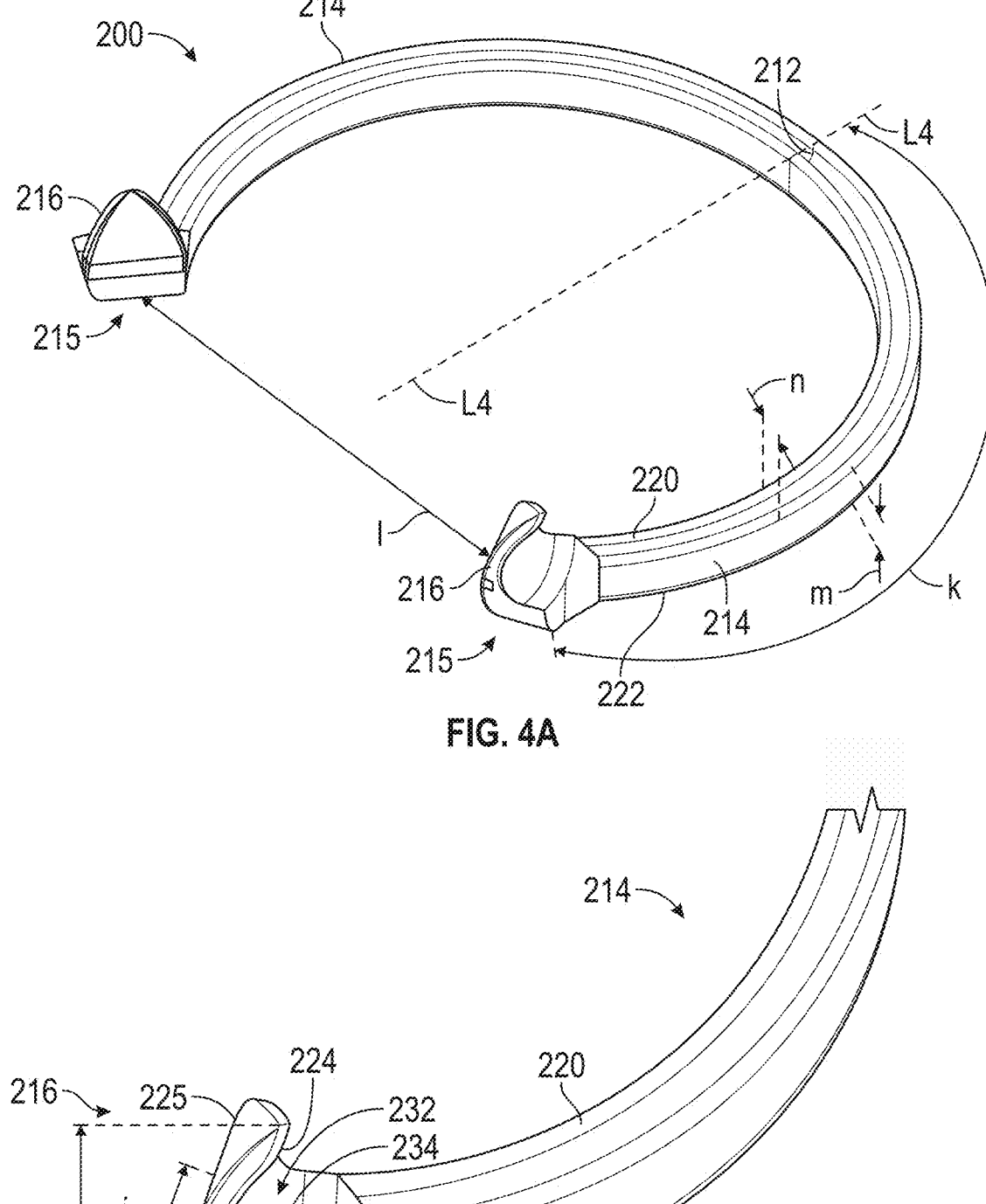
FIGS. 4A and 4B are perspective views of a second exemplary cranial spring.

Turning to FIGS. 4A and 4B, a second exemplary cranial spring 200 is shown and described. Specifically, the cranial spring 200 can comprise a generally circular body (or a partially circular or semi-circular body) including two opposing continuously curved arms 214 joined at and extending away from center portion 212. In some examples, each of the arms 214 has a continuous curvature from the center portion 212 to respective end portions 215. An opening in the circular body (disposed between end portions 215 of the arms 214 and thereby making the body a partial circle) opposes the center portion 212. Different from the spring 100, the spring 200 lacks a vertex portion and the arms 214 are curved rather than linear. The semi-circular configuration of the spring 200 can be configured to distribute the deforming force more evenly across the center portion and/or the arms of the spring (relative to a V-shaped or U-shaped spring), which can e.g., prevent failure or breaking of a polymer material of the spring (exemplary materials for the spring are discussed further below) when deformed.

Similar to the spring 100, the spring 200 further includes foot portions 216 disposed at the end portions 215 of each of the arms 214. In other words, a first foot portion 216 is disposed at a first end portion 215 of a first one of the arms 214, and a second foot portion 216 is disposed at a second end portion 215 of a second one of the arms 214. The foot portions 216 can be attached or formed on a first (lower) surface 220 of the distal end 215 of the arm 214 and extend inwardly or toward a longitudinal axis LA of the spring. When implanted the first (lower) surface 220 can be oriented toward the patient's brain, and an opposing second (upper) surface 222 can be oriented away from the patient's brain.

As can be seen in FIG. 4B, the foot portion 216 can be configured to form an abutment region or engagement portion of the spring 200 for contact with bone. In some examples, the foot portion 216 can include a base portion 218 that is substantially continuous with the arm 214 and a tapered, curved wall 225 that extends distally from the base 218 along a vertical axis (e.g., along a vertical axis that is perpendicular to the longitudinal axis L4 of the spring 200). The tapered curved wall 225 includes an interior proximal surface 228 that is coextensive with the first (lower) distal surface 220 of the arm 214, a central surface 234, and an interior distal (tip) surface 224, which cooperatively form a recess 232 (which can also be referred to as a channel, a receiving portion, or an engagement portion). In alternate examples, the curved wall 225 can have a continuous width such that the curved wall is not tapered.

When engaged with the skull bone, the interior proximal surface 228 and the interior distal surface 224 can be configured to respectively contact exterior and interior surfaces of the bone, and the central surface 234 can be configured to contact a side edge of the bone. Accordingly, the recess 232 of each foot portion 216 can be shaped and sized to engage or receive an edge of a skull bone along a sagittal suture gap. For example, one of the foot portions 216 can engage a first skull bone on a first side of a suture gap (such as, for example, the skull bone 22 on a first side of the suture gap 20 shown in FIG. 1B) for application of a first spring force thereon, and the other of the foot portions 216 can engage a second skull bone on an opposing side of the suture gap (such as, for example, the skull bone 24 on a second side of the suture gap 20 shown in FIG. 1B) for application of a second spring force thereon.

In some examples, the configuration of the foot portion 216 provides a wider surface area for contacting the bone at the top and side surfaces thereof relative to conventional cranial springs (such as, e.g., the cranial spring 10 shown in FIG. 1A). The relatively wider foot portion (for example, the wider central surface 234) enables distribution of the spring force across a greater surface area of bone relative to conventional cranial springs (which comprise a wire having a narrower width relative to a height thereof), thereby decreasing or limiting or eliminating the risk of bone shear or burrowing while implanted relative to conventional cranial springs. For example, as indicated in FIG. 4B, the surfaces that form the recess are sized such that the recess 232 can have a height h, a center width i, and a depth j. In some examples, the height h can be in a range from 2 mm to 10 mm, the width i can be in a range from 4 mm to 15 mm, and the depth j can be in a range from 2 mm to 10 mm. When implanted in the cranium of a patient, the width i can extend along the edge of the adjacent bone and the height h can be generally in the direction of the bone thickness. In some examples, the width i can be greater than the height h. For example, the width i can be in a range of 1.5 to 7.5 times greater than the height h, such as being 1.5 to 2 times greater, 1.5 to 3 times greater, 1.5 to 3.5 times greater, 2 to 3 times greater, etc.

Returning to FIG. 4A, each arm 214 has a circumferential length k, and the arms 214 define a distance/between the distal ends 215 of the arms 214 (which can be related to the length k) when the cranial spring is in the relaxed, unconstrained state. The opening or gap between the arms can have the dimension l. In one specific example, the length k can be in a range from 50 mm to 90 mm and the distance l can be in a range from 40 mm to 90 mm. Further, each of arms 214 has a height m and a width n. In some examples, the height m can be in a range from 2 mm to 6 mm and the width n can be in a range from 2 mm to 6 mm.

It will be appreciated that the foregoing dimensions are merely exemplary, and the recess 232 (and/or other portions of the foot portion 216), as well as the arms 214 can have other dimensions in alternate implementations.

In some examples, the foregoing dimensions can be selected to provide a specified force, a specified maximum spring expansion, and/or a specified distribution of spring force on bone. Further, in some examples, the foregoing features of the spring (dimensions) can have a known or quantifiable relationship to one another and be varied proportionally to meet the specified force, the specified maximum spring expansion, and/or the specified distribution of spring force on bone.

For example, where the length k is shorter, a potential spring force and/or a maximum spring expansion may be increased, and a width of the foot portion can be proportionally increased to meet a specified distribution of the spring force on bone. In another example, where length k is longer, a potential spring force and/or a maximum spring expansion may be decreased, and a width of the foot portion can be proportionally decreased to meet the specified of the spring force on bone.

In some examples, the cranial springs 100, 200 can be comprised of a bioresorbable material. In one specific example, the cranial springs 100, 200 can be comprised of Poly (D,L-lactide-co-glycolide), 85:15 (referred to as 85:15 PLGA), which has a sufficient material strength and elasticity (flexibility) to function as a spring and breaks down (reabsorbs) overtime after implantation. The bioresorbable material can be formed into the spring by various methods, such as, 3D printing, injection molding, or other methods. In alternate examples, the springs 100, 200 can be comprised of other bioresorbable materials. For example, the springs can be comprised of poly (E-caprolactone) and/or poly (butylene succinate).

In some examples, one or more of the dimensions of the spring described above can (at least in part) define a total mass of the spring, and therefore be selected to control or enable a specified resorption period of the spring. Further, in some examples, the springs can include one or more features that increase a surface area-to-volume of the spring and thereby enable an increased rate of resorption and/or a shortened resorption period, without decreasing other dimensions of the spring. Specifically, as can be seen in FIGS. 3A and 3B, the vertex portion 112 and the arms 114 can have one or more depressions or recessed portions (e.g., such as upper and/or lower channels that extend along the length of the device) that increase a surface area-to-volume ratio of the spring 100. Similarly, as can be seen in FIGS. 4A and 4B, the arms 214 can have one or more depressions or recessed portions that increase a surface area-to-volume ratio of the spring 200. An exemplary cross-section configuration that can be implemented in either of the arms 114, 214 and/or the center portion 112, 212 for variations of the springs 100, 200 is shown in FIG. 5.

Figure 5:
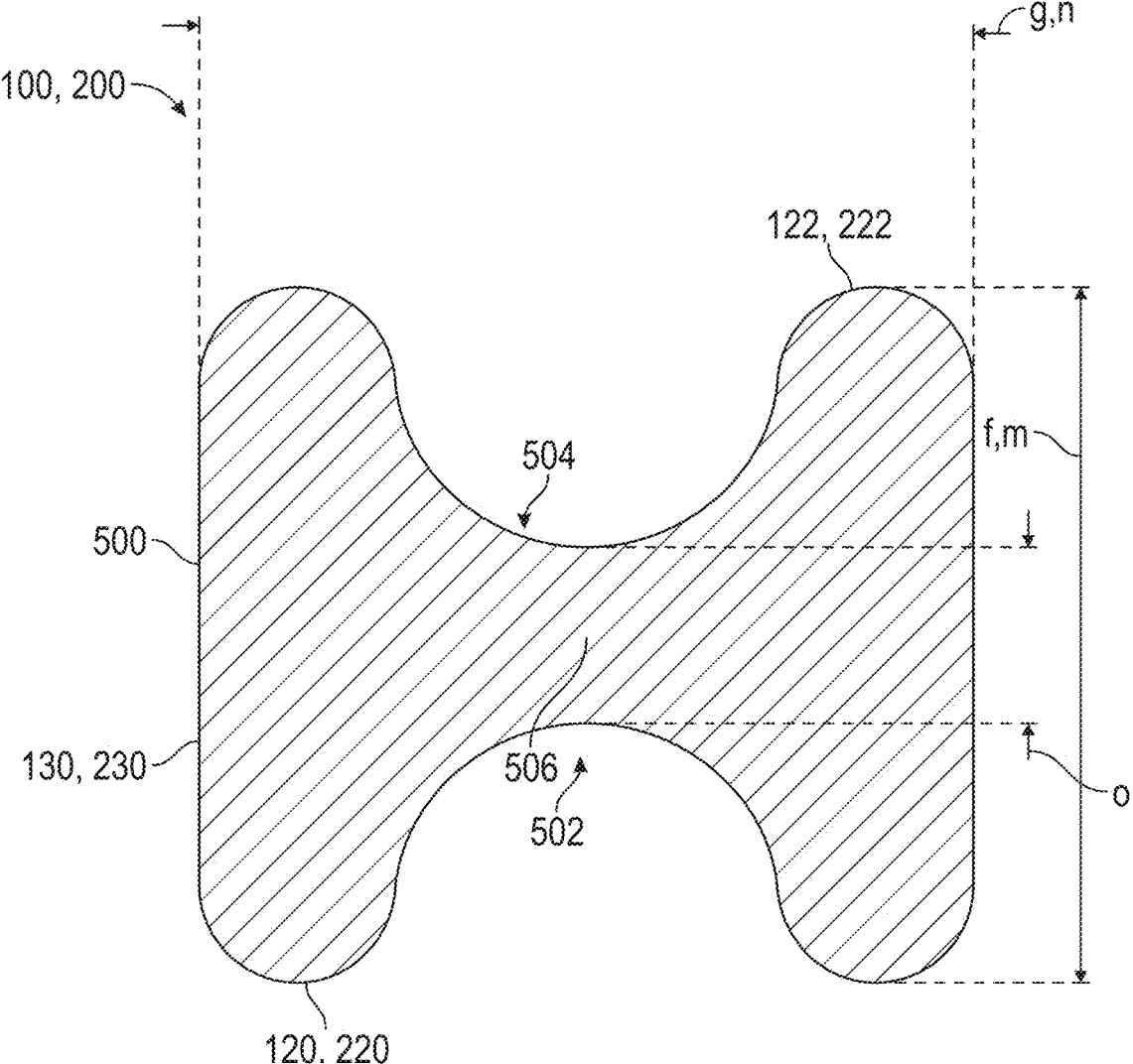
FIG. 5 is an exemplary cross-sectional configuration that can be implemented in variation so either of the first and second cranial springs.

Specifically, FIG. 5 illustrates that the arms 114, 214 of the springs 100, 200 can have a cross-section with an H-configuration 500. Although not specifically shown, the vertex portion 112 of the spring 100 can have a similar or identical H-configuration cross section. As can be seen in FIG. 5, the H-configuration 500 includes opposing recessed portions 502, 504 respectively (also referred to as channels) at the lower surface 120, 220 and the upper surface 122, 222 of the arm 114, 214. In the present example, each of the recessed portions 502, 504 has a similar or identical configuration relative to each other and comprises a generally continuously curved surface or a U-shaped surface that extends inwardly toward a center point of the arm 114, 214. A center portion 506 disposed between the recessed portions 502, 504 can have a height (e.g., thickness) o. In some examples, the height o can be in a range from 0.5 mm to 3 mm. In the illustrated example, the spring can include two outer portions or walls that are interconnected by the center portion 506 to form the H-shaped cross section.

In other examples, the cross section can have just one recessed portion and an opposing surface of the arm can be substantially flat. In yet other examples, the recessed portions can have other cross-sectional shapes, such as having a V-shaped or a rectangular-shaped the recessed portions. In still other examples, the recessed portions can have a different configuration relative to each other, for example, one recessed portion can have a greater depth than the other, or a different shape relative to the other. In even other examples, the center portion can have a greater height or thickness, such that the recessed portions are shallower.

The H-configuration 500 can reduce a total mass and increase a surface area of the spring 100 (increase a surface area-to-volume ratio) relative to, for example, a spring with a square or rectangular cross section configuration lacking any recessed portions. Further, the H-configuration can reduce a time period required for resorption and/or increase a rate of resorption of the springs 100, 200 after implantation.

In some examples, the springs 100, 200 can be configured to have a specified resorption period where the spring begins to break down or dissolve, for example, after approximately three months of implantation and can be configured to fully resorb, for example, after one year. It will be appreciated that the dimensions of the spring and features of the cross-sectional shape discussed above can be selected to enable the targeted resorption period.

Methods

In exemplary implantation methods, a portion of a skull of a patient can be accessed through an incision and at least a portion of an abnormal suture can be excised to form a suture gap. A cranial spring, such as one of the cranial springs 100, 200, can be implanted in the suture gap in a compressed or deformed state where the arms 114, 214 of the spring are compressed toward each other. In some examples, the longitudinal axis of the spring is aligned with suture gap. In some examples, the implanting includes engaging a first foot portion 116, 216 of the spring 100, 200 with an edge portion of a first skull bone of the suture gap and engaging a second foot portion 116, 216 of the spring 100, 200 with an edge portion of a second skull bone of the suture gap. For example, a recess 132, 232 of the respective foot portions 116, 216 can be hooked over or fitted around or over an edge of a skill bone such that a central surface 134, 234 is abutted to an edge portion of the skull bone. In some examples, a width of the sagittal suture gap can be less than a distance between the distal ends 115, 215 of the arms 114, 214 when the spring 100, 200 is in the relaxed, unconstrained state. Dimensions of the springs 100, 200 (such as those discussed above) and/or material strength of the spring 100, 200 can be selected such that the spring acts on the skull bones with a known force (for example, a force in a range of 1.5-10 N) in a direction away from the longitudinal axes L2, L4 of the spring. In some examples, one or more (e.g., one, two, or three) of the springs 100, 200 can be implanted along the sagittal suture gap. After implantation of the one or more springs, the incision can be closed.

While implanted, the first foot portion can apply a first spring force distributed over a portion of the edge of the first skull bone and the second foot portion can apply a second spring force distributed over a portion of the edge of the second skull bone. Over time, the implanted spring(s) 100, 200 function to widen the skull in a direction generally perpendicular to the axis of the excised suture, while minimizing, limiting or preventing bone shear of the first skull bone and the second skull bone. As the spring(s) 100, 200 expand, they can normalize the head shape and create more space along the sagittal suture. The implanted spring(s) 100,

200 begin to break down or dissolve, for example, after approximately three months of implantation and can be fully resorbed, for example, after one year. Therefore, in some examples, the implanted spring(s) 100, 200 will not require an additional (second) surgery for removal from the patient.

Figure 6:
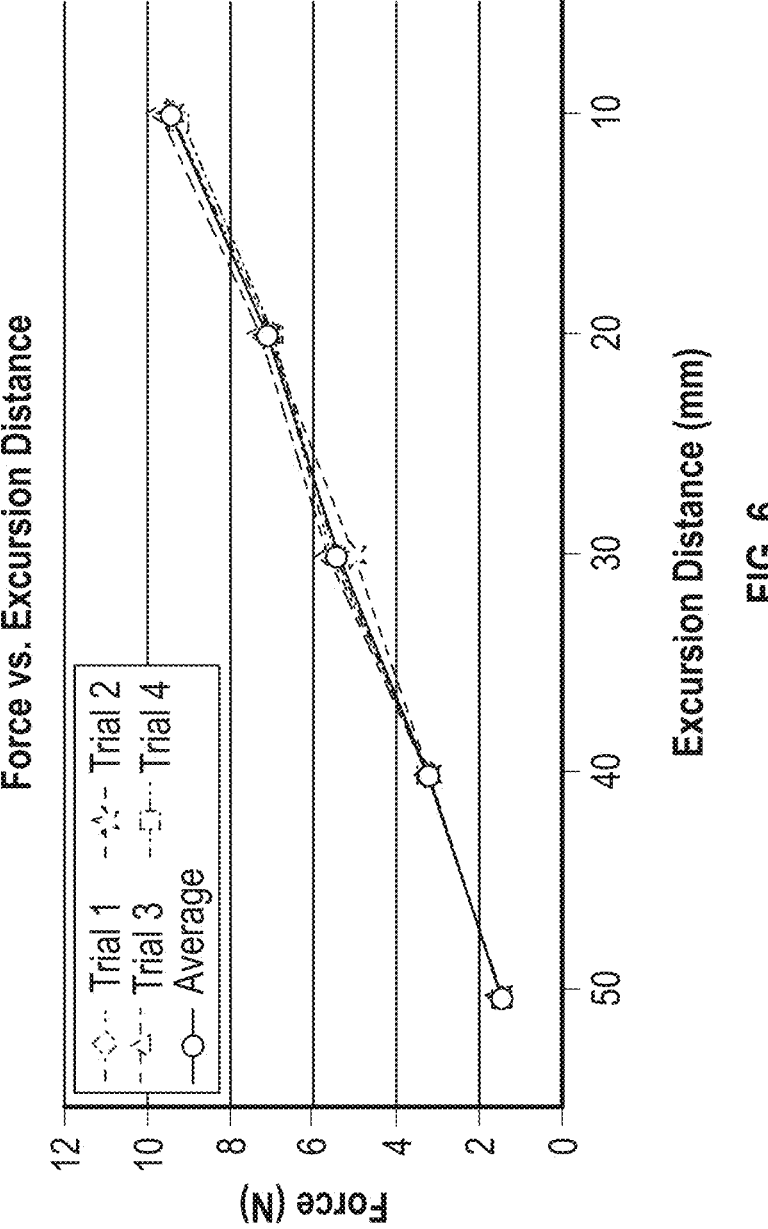
FIG. 6 is a graph showing force-displacement curves for various bioresorbable cranial springs.

Exemplary force-displacement data for cranial springs disclosed herein (such as, the cranial springs 100, 200) made from Poly (D,L-lactide-co-glycolide), 85:15 (85:15 PLGA) and configured for implantation in a sagittal suture gap are graphically illustrated in FIG. 6. Specifically, FIG. 6 includes a force-displacement curve for each of four trials, and an average force-displacement curve of the four trials. The data shown in FIG. 6 illustrate that the force displacement of properties of the cranial springs disclosed herein (such as, the cranial springs 100, 200) approximate the force-displacement properties of conventional steel cranial springs (such as those discussed above with reference to FIGS. 1A, 1B, 2B, and 2C).

In other examples, the bioresorbable cranial springs can be implanted along other cranial sutures (e.g., a frontal suture) for treatment of other forms of craniosynostosis. In still other examples, the bioresorbable springs can be implanted in other regions of the body that require separation of bones.

In yet other examples, the springs 100, 200 can be comprised of non-resorbable materials and can instead be removed from a patient via a second surgical procedure.

In view of the many possible embodiments to which the principles of the disclosed technology may be applied, it should be recognized that the illustrated embodiments are only preferred examples and should not be taken as limiting the scope of the disclosure. Further, the exemplary springs can include features of other examples disclosed herein. For example, the spring 100 can include foot portions having a configuration similar to the foot portions 216, or the spring 200 can include foot portions having a configuration similar to the foot portion 116. In another example, the springs 100, 200 can be configured to be implanted in an overlapping configuration, as illustrated with the springs 10, 10' shown FIG. 1B, or in other orientations or configurations.

The scope of the disclosure is at least as broad as the following exemplary claims and equivalents of the recited features.

The invention claimed is:

1. A cranial spring comprising:
   a first arm and a second arm, each of the first arm and the second arm joined at a center portion, wherein the first arm comprises a first end portion and the second arm comprises a second end portion, wherein a gap is disposed between the first end portion and the second end portion; and
   a first foot portion disposed at the first end portion, and a second foot portion disposed at the second end portion;
   wherein the first foot portion comprises a first recess sized and shaped to receive an edge of a first skull bone, and the second foot portion comprises a second recess sized and shaped to receive an edge of a second skull bone;
   wherein a first bone abutment surface of the first recess is sized and shaped to engage the edge of the first skull bone, and a second bone abutment surface of the second recess is sized and shaped to engage the edge of the second skull bone, wherein the first bone abutment surface has a first width and the second bone abutment surface has a second width;
   wherein the first width of the first bone abutment surface is greater than a first height of the first bone abutment surface, and the second width of the second bone abutment surface is greater than a second height of the second bone abutment surface; and wherein the cranial spring comprises a bioresorbable material.

2. The cranial spring of claim 1, wherein the first width is in a range of 1.5 to 7.5 times greater than the first height, and the second width is in a range of 1.5 to 7.5 times greater than the second height.

3. The cranial spring of claim 1, wherein each of the first width and the second width is in a range of 4 mm to 15 mm.

4. The cranial spring of claim 1, wherein each of the first arm and the second arm is curved and forms a semi-circular-shaped body of the cranial spring.

5. The cranial spring of claim 1, wherein the center portion comprises a curved vertex portion and each of the first arm and the second arm is linear, and wherein the curved vertex portion, the first arm, and the second arm form a V-shaped or U-shaped body of the cranial spring.

6. The cranial spring of claim 1, wherein one or more of the first arm or the second arm comprises an H-configuration cross-section.

7. The cranial spring of claim 1, wherein each of the first bone abutment surface and the second bone abutment surface is sized and shaped such that, when the cranial spring is implanted, the cranial spring applies a first spring force on the first skull bone and a second spring force on the second skull bone.

8. The cranial spring of claim 7, wherein each of the first bone abutment surface and the second bone abutment surface is sized and shaped such that, when the cranial spring is implanted, a distribution of the first spring force across a portion of the first skull bone limits shear of the first skull bone and a distribution of the second spring force across a portion of the second skull bone limits shear of the second skull bone.

9. The cranial spring of claim 1, wherein the cranial spring is sized and shaped for implantation within a suture gap and beneath a skin surface, wherein the suture gap is between the first skull bone and the second skull bone.

10. The cranial spring of claim 1, wherein the cranial spring is configured to dissolve over a resorption period within a patient without surgical removal of the cranial spring, wherein the resorption period is within a range of three months to one year.

11. The cranial spring of claim 10, wherein the cranial spring has a surface area-to-volume ratio that enables the cranial spring to fully resorb within the resorption period.

12. The cranial spring of claim 1, wherein the bioresorbable material comprises poly (D,L-lactide-co-glycolide) (PLGA).

13. A bioresorbable cranial spring comprising:

a first arm and a second arm, each of the first arm and the second arm joined at a center portion, wherein the first arm comprises a first end portion and the second arm comprises a second end portion, wherein a gap is disposed between the first end portion and the second end portion;

wherein each of the first arm and the second arm has a first height and a first width; and wherein one or more of the first arm or the second arm comprises an H-configuration cross-section configured to increase a surface area-to-volume ratio of the bioresorbable cranial spring relative to a rectangular cross-section having the first height and the first width.

14. The bioresorbable cranial spring of claim 13, wherein the first end portion comprises a first bone abutment surface and the second end portion comprises a second bone abutment surface; and wherein each of the first bone abutment surface and the second bone abutment surface is sized and shaped such that, when the cranial spring is implanted, the cranial spring applies a first spring force on a portion of a first skull bone and a second spring force on a portion of a second skull bone.

15. The bioresorbable cranial spring of claim 14, wherein a width of each of the first bone abutment surface and the second bone abutment surface is greater than a respective height thereof.

16. The bioresorbable cranial spring of claim 13, wherein the first arm, the second arm, and the center portion form a V-shaped or U-shaped body.

17. The bioresorbable cranial spring of claim 13, wherein the first arm, the second arm, and the center portion form a semi-circular-shaped body.

18. A cranioplasty method comprising:

accessing a skull of a patient through an incision;

excising an abnormal suture to form a suture gap;

implanting one or more bioresorbable cranial springs of claim 13 within the suture gap such that a longitudinal axis of the one or more bioresorbable cranial springs is aligned with the suture gap;

closing the incision; and allowing the one or more bioresorbable cranial springs to dissolve over a resorption period within the patient without surgical removal of the one or more bioresorbable cranial springs.

19. The cranioplasty method of claim 18, wherein the implanting comprises deforming the first arm and the second arm of each of the one or more cranial springs toward the longitudinal axis of the respective cranial spring, engaging a first foot portion of the first arm with a first skull bone, and engaging a second foot portion of the second arm with a second skull bone, wherein the first foot portion and the second foot portion are each sized and shaped such that, when the respective cranial spring is implanted, a distribution of a first spring force exerted by the first foot portion across a portion of an edge of the first skull bone limits shearing of the first skull bone and a distribution of a second spring force exerted by the second foot portion across a portion of an edge of the second skull bone limits shearing of the second skull bone.

20. A bioresorbable cranial spring comprising:

a first arm and a second arm, each of the first arm and the second arm joined at a center portion, wherein the first arm comprises a first end portion and the second arm comprises a second end portion, a gap disposed between the first end portion and the second end portion; and a first foot portion disposed at the first end portion, and a second foot portion disposed at the second end portion;

wherein a first bone abutment surface of the first foot portion is sized and shaped to engage a first skull bone, and a second bone abutment surface of the second foot portion is sized and shaped to engage a second skull bone, wherein the first bone abutment surface has a first width and the second bone abutment surface has a second width;

wherein the first foot portion is configured to engage an edge of the first skull bone along the first width, and the second foot portion is configured to engage an edge of the second skull bone along the second width;

wherein each of the first width and the second width is in a range of 4 mm to 15 mm; and wherein the first width of the first bone abutment surface is in a range of 1.5 to 7.5 times greater than a first height of the first bone abutment surface, and the second width of the second bone abutment surface is in a range of 1.5 to 7.5 times greater than a second height of the second bone abutment surface; and wherein the bioresorbable cranial spring comprises a bioresorbable material and is configured to dissolve over a resorption period after implantation within a patient.

\* \* \* \* \*